US00PP11734P2

(12) United States Plant Patent
van Rijn

(10) Patent No.: US PP11,734 P2
(45) Date of Patent: Jan. 2, 2001

(54) ANTHURIUM PLANT NAMED 'CANDY LOVE'

(75) Inventor: Leonardus van Rijn, Schipluiden (NL)

(73) Assignee: Rijnplant, Schipluiden (NL)

( * ) Notice: Under 35 U.S.C. 154(b), the term of this patent shall be extended for 0 days.

(21) Appl. No.: 09/291,109

(22) Filed: Apr. 14, 1999

(51) Int. Cl.[7] ..... A01H 5/00
(52) U.S. Cl. ..... Plt./365
(58) Field of Search ..... Plt./369, 365, 367, Plt./368

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Anthurium plant named 'Candy Love', characterized by its upright and outwardly spreading plant habit; freely clumping, dense and bushy growth habit; durable dark green leaves that are ovate to lanceolate in shape; numerous inflorescences that are positioned upright and beyond the foliage on strong and erect scapes; durable, glossy light red spathes; year-round continuous flowering; and good post-production longevity.

1 Drawing Sheet

BACKGROUND OF THE INVENTION

The present invention relates to a new and distinct cultivar of Anthurium plant, botanically known as *Anthurium andreanum*, and hereinafter referred to by the cultivar name Candy Love.

The new Anthurium is a product of a planned breeding program conducted by the Inventor in Schipluiden, The Netherlands. The objective of the program is to create and develop new Anthurium cultivars that have a freely clumping growth habit, strong and vigorous plant growth, attractive spathe color, numerous inflorescences and leaves, and good post-production longevity.

The new Anthurium originated from a cross by the Inventor on Mar. 2, 1994, in a laboratory in Belgium, of the Inventor's proprietary *Anthurium andreanum* selection code number 92-8 as the female, or seed, parent with the Inventor's proprietary *Anthurium andreanum selection code number* 92-3 as the male, or pollen, parent. The cultivar Candy Love was discovered and selected by the Inventor as a plant within the progeny of the stated cross in a controlled environment in Schipluiden, The Netherlands in June, 1996.

Asexual propagation of the new cultivar by tissue culture has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits has been repeatedly observed and are determined to be the unique characteristics of the cultivar Candy Love. There characteristics in combination distinguish 'Candy Love' as a new and distinct cultivar:

1. Upright and outwardly spreading plant habit.
2. Freely clumping, dense and bushy growth habit.
3. Durable dark green leaves that are ovate to lanceolate in shape.

4. Numerous inflorescences that are positioned upright and beyond the foliage on strong and erect scapes.
5. Durable, glossy light red spathes.
6. Year-round continuous flowering.
7. Good post-production longevity.

The new Anthurium can be compared to the female parent, the Inventor's proprietary selection code number 92-8. In side-by side comparisons conducted by the Inventor in Schipluiden, The Netherlands, plants of the new Anthurium differ from plants of selection code number 92-8 in the following characteristics:

1. Plants of the new Anthurium are more compact than plants of the selection code number 92-8.
2. Plants of the new Anthurium are more freely clumping than plants of the selection code number 92-8.
3. Plants of the new Anthurium have lighter red-colored spathes than plants of the selection code number 92-8.

The new Anthurium can be compared to the male parent, the Inventor's proprietary selection code number 92-3. In side-by-side comparisons conducted by the Inventor in Schipluiden, The Netherlands, plants of the new Anthurium differ from plants of selection code number 92-3 in the following characteristics.

1. Plants of the new Anthurium are more compact than plants of the selection code number 92-3.
2. Plants of the new Anthurium are more freely clumping than plants of the selection code number 92-3.
3. Plants of the new Anthurium have smaller leaves than plants of the selection code number 92-3.
4. Plants of the new Anthurium have smaller spathes than plants of the selection code number 92-3.

The new Anthurium can be compared to the Anthurium cultivar Champion, disclosed in U.S. Plant Pat. No. 9,088. In side-by-side comparisons conducted by the Inventor in Schipluiden, The Netherlands, plants of the new Anthurium differ from plants of the cultivar Champion in the following characteristics:

1. Plants of the new Anthurium grow faster than plants of the cultivar Champion.
2. Plants of the new Anthurium are more freely clumping than plants of the cultivar Champion.

3. Plants of the new Anthurium have rougher leaves than plants of the cultivar Champion.
4. Plants of the new Anthurium and of the cultivar Champion differ in spathe shape.

BRIEF DESCRIPTION OF THE PHOTOGRAPH

The accompanying colored photograph illustrates the overall appearance of the new Anthurium, showing the colors as true as it is reasonably possible to obtain in colored reproductions of this type. The photograph comprises a side perspective view of a typical potted plant of the cultivar Candy Love. Leaf, spathe and spadix colors in the photograph may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe one-year old plants in 14-cm containers grown in Schipluiden, The Netherlands, in a glass greenhouse with an average day temperature of 25° C. and an average night temperature of 19° C.

Botanical classification: *Anthurium andreanum* cultivar Candy Love.

Parentage:

*Female parent*.—Inventor's proprietary *Anthurium andreanum* selection code number 92-8.

*Male parent*.—Inventor's proprietry *Anthurium andreanum* selection code number 92-3.

Propagation:

*Method*.—Typically by tissue culture.

*Time to initiate roots*.—About 70 or 84 days at 24° C. or 21° C., respectively, from a tissue cultured plantlet in a laboratory in Belgium.

*Rooting habit*.—Numerous and very strong fleshy roots.

Plant description:

*Plant shape*.—Upright and outwardly spreading, inverted triangle, symmetrical.

*Growth habit*.—Freely clumping, bushy and dense, about six to eight shoots per plant. Appropriate for 12 to 20-cm containers.

*Plant height*.—About 40 cm from soil level to leaf plane and about 50 cm from soil level to apex of spathes.

*Plant width*.—About 40 to 50 cm.

*Plant vigor*.—High.

*Growth rate*.—Rapid.

*Crop time*.—About 6 and 12 months are usually required from planting of young plants to finished plants in 12 and 20-cm containers, respectively.

*Foliage description*.—Quantity: Usually about five to six leaves per shoot; about 30 to 48 leaves per container. Length: About 14 to 18 cm. Width: About 6 to 10 cm. Shape: Ovate to lanceolate. Apex: Apiculate to aristate. Base: Auriculate; lobes not overlapping. Margin Entire. Texture: Smooth, glabrous, leathery. Color: Young leaves, upper surface: 144B. Young leaves, lower surface: More gray than 144C. Mature leaves, upper surface: 147A. Mature leaves, lower surface: Close to 146A. Petiole: Length: About 20 to 33 cm. Color: Close to between 144A and 146A. Geniculum length: About 1.5 to 2.5 cm; slightly longer on older peduncles. Geniculum diameter: About 3 to 5 mm. Geniculum color: 144B.

Inflorescence description:

*Inflorescence arrangement*.—Spathes with spadices held beyond the foliage. Flowering structures arise from leaf axils. Freely flowering; continuous flowering year-round; numerous spathes/spadices per plant.

*Inforescence longevity*.—Spathes/spadices last about six weeks under winter conditions and about three months under summer conditions; persistent.

*Flowers*.—Quantity per spadix: Numerous, about 200. Shape: Rounded. Diameter: About 1 mm, maximum.

*Spathe*.—Length: About 6 to 9 cm. Width: About 9 to 12 cm. Shape: Very broadly cordate. Apex: Apiculate to cuspidate. Base: Rounded to straight. Margin: Entire. Texture: Leathery, glabrous, moderate blistering, glossy. Color: When opening: 48B. Front surface: 47B. Back surface: 48C. After senescence: 47B and becoming overlaid with dark greenish red.

*Spadix*.—Length: About 6 to 9 cm. Diameter: Midsection, about 8 mm; apex, about 5 mm. Shape: Columnar. Longitudinal axis: Very weakly recurved. Color: Base: 49D. Mid-section: 48C. Apex: 40D to 44D. Color, after senescence: 146C.

*Scape*.—Length: About 30 to 40 cm. Aspect: Strong and erect. Color: 144A to 146A.

*Reproductive organs*.—Androecium: Pollen color: Creamy white, 158D. Gynoecium: Stigma shape: Ovoid. Ovary: Protogynous.

Disease resistance: Plants of the new Anthurium have exhibited resistance to root diseases common to Anthurium.

Seed development: Seed development on plants of the new Anthurium has not been observed.

It is claimed:

1. A new and distinct cultivar of Anthurium plant named 'Candy Love', as illustrated and described.

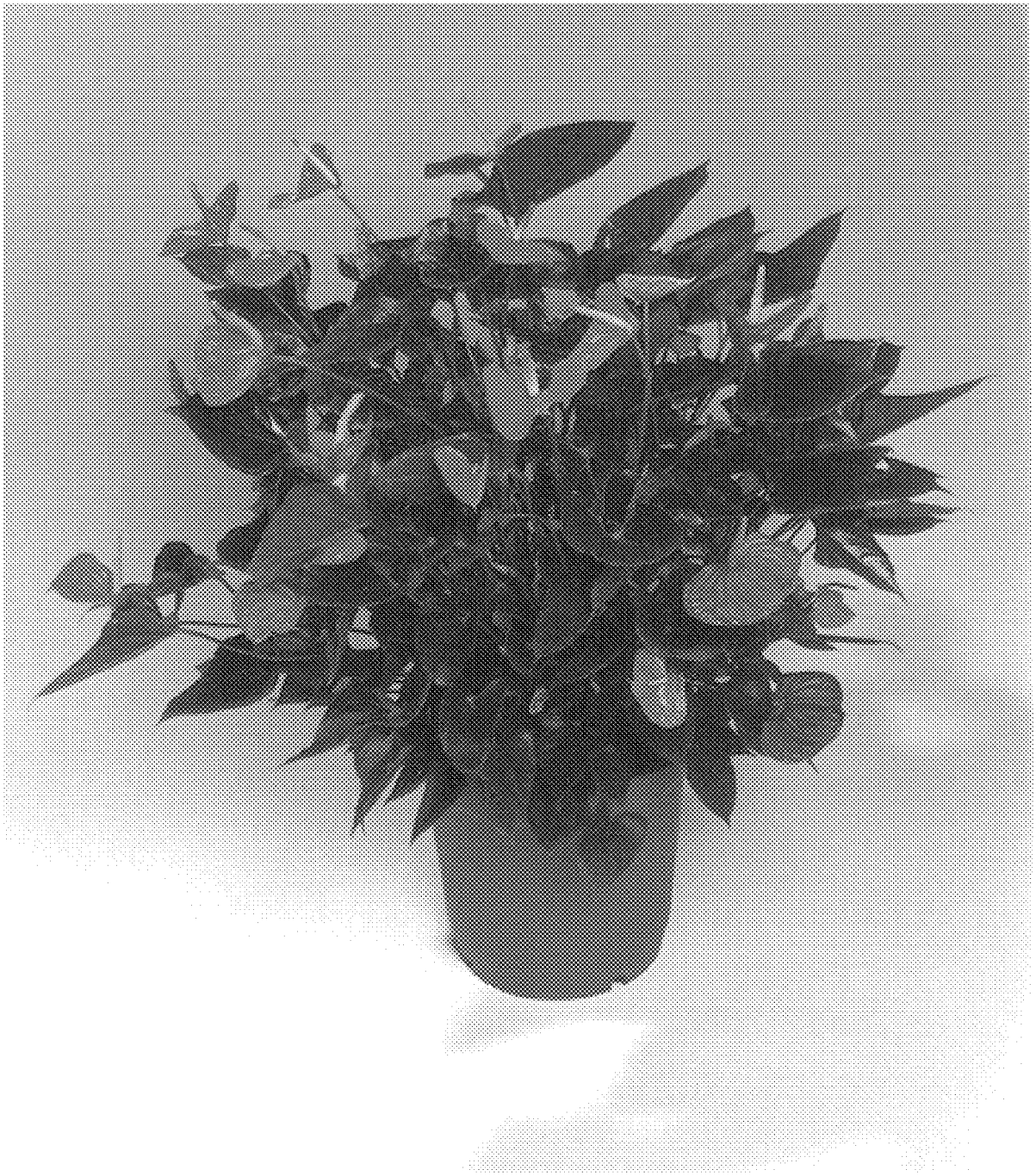

* * * * *